US010881808B2

(12) United States Patent
Säll

(10) Patent No.: US 10,881,808 B2
(45) Date of Patent: Jan. 5, 2021

(54) MEDICAMENT DELIVERY DEVICE WITH VIBRATION SENSOR

(71) Applicant: CAREBAY EUROPE LTD, Sliema (MT)

(72) Inventor: Daniel Säll, Segeltorp (SE)

(73) Assignee: SHL MEDICAL AG, Zug (CH)

(*) Notice: Subject to any disclaimer, the term of this patent is extended or adjusted under 35 U.S.C. 154(b) by 277 days.

(21) Appl. No.: 15/767,460

(22) PCT Filed: Oct. 6, 2016

(86) PCT No.: PCT/EP2016/073836
§ 371 (c)(1),
(2) Date: Apr. 11, 2018

(87) PCT Pub. No.: WO2017/071927
PCT Pub. Date: May 4, 2017

(65) Prior Publication Data
US 2018/0296767 A1 Oct. 18, 2018

(30) Foreign Application Priority Data
Oct. 30, 2015 (EP) .................................... 15192312

(51) Int. Cl.
A61M 5/315 (2006.01)

(52) U.S. Cl.
CPC .... A61M 5/31568 (2013.01); A61M 5/31566 (2013.01); A61M 2205/3375 (2013.01);
(Continued)

(58) Field of Classification Search
CPC .... A61M 5/24; A61M 5/315; A61M 5/31525; A61M 5/3155; A61M 5/31551;
(Continued)

(56) References Cited

U.S. PATENT DOCUMENTS

2002/0143288 A1* 10/2002 Larsen ............. A61M 5/31551
604/19
2004/0171983 A1 9/2004 Sparks
(Continued)

FOREIGN PATENT DOCUMENTS

TW 201350158 A 12/2013
WO 02/064196 A1 8/2002
(Continued)

OTHER PUBLICATIONS

International Search Report and Written Opinion for Int. App. No. PCT/EP2016/073836, completed Jan. 3, 2017.

Primary Examiner — Laura A Bouchelle
Assistant Examiner — Anh Bui
(74) Attorney, Agent, or Firm — McDonnell Boehnen Hulbert & Berghoff LLP

(57) ABSTRACT

A button-activated medicament delivery device is presented having a housing arranged to house a medicament container, a vibration sensor configured to measure vibrations induced by the button-activated medicament delivery device during a medicament delivery, a button arranged to initiate medicament delivery from the medicament container, and to activate the vibration sensor when initiating the medicament delivery, and processing circuitry configured to obtain a vibration measurement from the vibration sensor and to compare the vibration measurement with a reference vibration measurement characteristic for the button-activated medicament delivery device during medicament delivery. The processing circuitry is configured to generate a time of measurement of the vibration measurement in case the vibration measurement matches the reference vibration measurement.

13 Claims, 6 Drawing Sheets

(52) U.S. Cl.
CPC ............... *A61M 2205/3569* (2013.01); *A61M 2205/3576* (2013.01); *A61M 2205/3584* (2013.01); *A61M 2205/50* (2013.01); *A61M 2205/52* (2013.01); *A61M 2205/582* (2013.01); *A61M 2205/8206* (2013.01)

(58) Field of Classification Search
CPC .......... A61M 5/31573; A61M 2205/50; A61M 2205/581; A61M 2205/582; A61M 2005/3125
See application file for complete search history.

(56) References Cited

U.S. PATENT DOCUMENTS

| | | | | |
|---|---|---|---|---|
| 2006/0135907 | A1* | 6/2006 | Remde | ................... G01N 29/14 604/67 |
| 2015/0290396 | A1* | 10/2015 | Nagar | ............... A61M 5/31535 340/540 |
| 2017/0189625 | A1* | 7/2017 | Cirillo | ............... A61M 5/31525 |
| 2017/0239468 | A1* | 8/2017 | Lemke | ............... A61K 31/4468 |

FOREIGN PATENT DOCUMENTS

| | | |
|---|---|---|
| WO | 2007/107564 A1 | 9/2007 |
| WO | 2015/136513 A1 | 9/2015 |

\* cited by examiner

MEDICAMENT DELIVERY DEVICE WITH VIBRATION SENSOR

CROSS REFERENCE TO RELATED APPLICATIONS

The present application is a U.S. National Phase application pursuant to 35 U.S.C. § 371 of International Application No. PCT/EP2016/073836 filed Oct. 6, 2016, which claims priority to European Patent Application No. 15192312.5 filed Oct. 30, 2015. The entire disclosure contents of these applications are herewith incorporated by reference into the present application.

TECHNICAL FIELD

The present disclosure generally relates to medical devices. In particular, it relates to a medicament delivery device of the type that includes a vibration sensor.

BACKGROUND

Medicament delivery devices such as auto-injectors, inhalers and eye-dispensers nowadays provide possibilities for the users themselves to handle medicament delivery in an easy, safe and reliable manner. Moreover, such devices also facilitate the administration of drugs for hospital personnel.

This freedom for patients to handle medicament delivery themselves has lead to the concept of adherence, or compliance, to become an increasingly important area in treatment of illnesses. Adherence involves monitoring of a patient's medication administration scheme as prescribed by a physician and evaluation of whether a prescribed medicament and medicament administration scheme has been successful or not in treating the illness of the patient.

It has been found that it is relatively common that a user does not administer the medication as prescribed. Reasons for a patient's failure to comply with the prescribed scheme include forgetfulness, pain associated with drug administration or discomfort experienced from side effects of the medication.

Failure to comply with a drug administration scheme may result in that the patient can experience poor recovery from an illness, and it may furthermore result in secondary diseases requiring additional medical attention. This may in turn bring unnecessary pressure on the healthcare system.

In view of the above, it is in the interest of both patients' and the healthcare to facilitate monitoring to increase the occurrences of medicament administration as prescribed.

WO2007/107564 A1 discloses an electronic module for mechanical medication delivery devices, and aims at monitoring the operation of a medication delivery device. This document discloses an electronic module that is attached onto a medication delivery device. The electronic module is capable of measuring acoustical and/or vibrational signals generated in response to relative movements of internal parts of the medication delivery device to which the electronic module is attached. Such internal parts can be mechanical parts which during movement generate for example acoustical sounds, such as click sounds. The electronic module is powered by a built-in battery which powers the module when for example a capacitive touch pad is activated. This activation is performed when for example a finger tip is positioned on the touch pad.

A disadvantage with the electronic module disclosed in WO2007/107564 A1 is that there is a risk that not all instances of drug administration will be recorded, and the electronic module could therefore provide an inaccurate picture for the purpose of adherence.

SUMMARY

In WO2007/107564 A1 the battery and thus the electronic module is activated provided a user touches the touch pad located on the electronic module. This touch pad is not associated with the mechanical operation of the medication delivery device. There is hence a risk that a user will forget to activate the electronic module prior to drug administration. This would result in that the following drug administration would not be registered.

In view of the above, a general object of the present disclosure is to provide a button-activated medicament delivery device that solves or at least mitigates the problems of the prior art.

There is hence provided a button-activated medicament delivery device comprising: a housing arranged to house a medicament container, a vibration sensor configured to measure vibrations induced by the button-activated medicament delivery device during a medicament delivery, a button arranged to initiate medicament delivery from the medicament container, and to activate the vibration sensor when initiating the medicament delivery, and processing circuitry configured to obtain a vibration measurement from the vibration sensor and to compare the vibration measurement with a reference vibration measurement characteristic for the button-activated medicament delivery device during medicament delivery, wherein the processing circuitry is configured to generate a time of measurement of the vibration measurement in case the vibration measurement matches the reference vibration measurement.

Since the vibration sensor is activated by the button that also initiates medicament delivery, it may be ensured that vibration measurements will be obtained any time drug administration is initiated.

One embodiment comprises a storage unit configured to store the time of measurement.

One embodiment comprises a transmitter configured to wirelessly transmit the time of measurement.

One embodiment comprises an activation switch switchable between an open state, and a closed state enabling powering of the vibration sensor, wherein the button is arranged to set the activation switch in the closed state upon initiation of medicament delivery.

According to one embodiment the processing circuitry is configured to compare amplitude and frequency content of the vibration measurement with amplitude and frequency content of the reference vibration measurement.

One embodiment comprises an energy storage unit configured to power the vibration sensor.

One embodiment comprises a circuit board arranged parallel to the energy storage unit, a first electrode defining a first electric pole and a second electrode defining a second electric pole, wherein the first electrode distances the circuit board from the energy storage unit.

One embodiment comprises an energy accumulation member, wherein the energy accumulation member is arranged to bias the button away from the activation switch. The activation switch will therefore normally be in the open state. This ensures that the energy storage unit will only feed power to the vibration sensor during drug administration, as this is the only situation when the activation switch will be in the closed state.

It may be noted that the biasing force provided by the energy accumulation member is lower than the force necessary to initiate medicament delivery. The stiffness of the energy accumulation member is hence selected such that the energy accumulation member is compressed sufficiently to enable the button to activate the vibration sensor when medicament delivery is initiated.

One embodiment comprises a plate member having a through-opening, which plate member is arranged between the circuit board and the button, wherein the energy accumulation member is arranged between the plate member and the button.

According to one embodiment the activation switch is aligned with the through-opening of the plate member and wherein the button has an actuation member aligned with the through-opening, which actuation member is arranged to actuate the activation switch.

According to one embodiment the vibration sensor, the button, and the processing circuitry form part of an activation button assembly that is releasably attached to the remainder of the button-activated medicament delivery device.

According to one embodiment the vibration sensor includes an acceleration sensor.

According to one embodiment the button-activated medicament delivery device is an injector.

One embodiment comprises a plunger rod, wherein the vibration sensor, the button and the processing circuitry form part of the plunger rod.

According to one embodiment the button activated medicament delivery device is an inhalator or an eye dispenser.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

Figure 1:
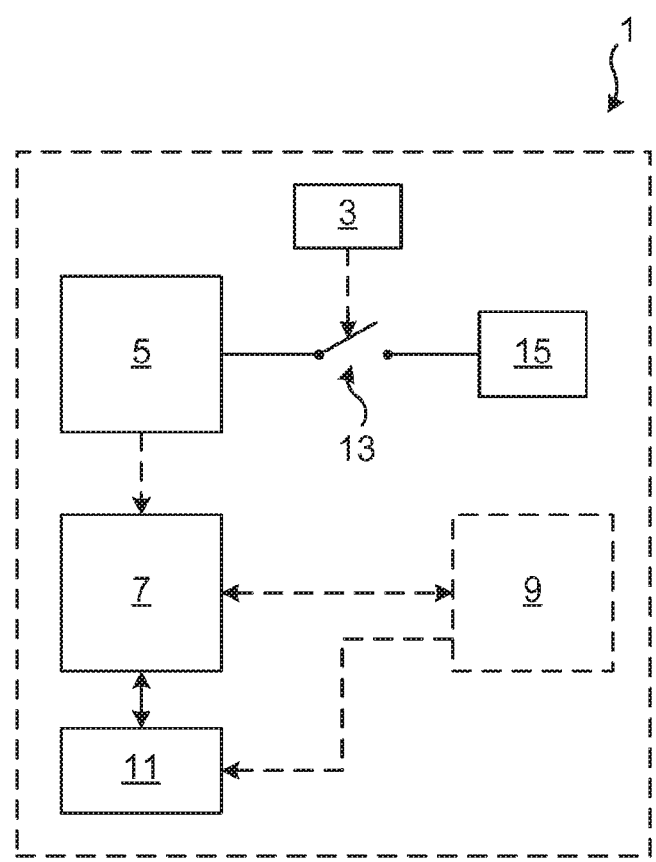
FIG. 1 shows a block diagram of a button-activated medicament delivery device.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The button-activated medicament delivery device disclosed herein facilitates monitoring of use thereof. With the term "use" is here meant the procedure of medicament expulsion or, equivalently, drug administration or medicament delivery.

The button-activated medicament delivery device disclosed herein may be a disposable medicament delivery devices or re-useable medicament delivery device. The button-activated medicament delivery device may for example be an injector, i.e. a manual injector or an auto-injector, an inhaler or an eye dispenser.

The button-activated medicament delivery device disclosed herein comprises a housing arranged to accommodate a medicament container containing a medicament. It furthermore comprises a button arranged to initiate medicament delivery from the medicament container, a vibration sensor arranged to be activated by the button upon the initiation of medicament delivery, and processing circuitry. The vibration sensor may include for example one or more acceleration sensors and/or a microphone.

The button is directly or indirectly mechanically coupled to the medicament container. Actuation of the button commences a mechanical interaction which leads to expulsion of medicament contained in the medicament container. Moreover, this actuation of the button also activates the vibration sensor, enabling the vibration sensor to measure vibrations induced by the button-activated medicament delivery device during medicament delivery. The vibration sensor is hence configured to measure the vibrations induced by the button-activated medicament delivery device during a medicament delivery.

The vibrations induced during drug administration are characteristic for medicament delivery and lead to characteristic mechanical waves. The vibrations are induced by the mechanical interaction between components of the button-activated medicament delivery device. Such vibrations may for example be induced by one or more "click" sounds generated during drug administration in the case of injectors. Such "click" sounds may for auto-injectors for example include a so-called end-of-injection feedback which provides the user with an audible indication as well as tactile indication, in the form of vibrations, that drug administration has finalised, or by a characteristic sound of an inhaler or eye dispenser when its content is expelled.

The processing circuitry is configured to compare a vibration measurement obtained from the vibration sensor, with a reference vibration measurement that is characteristic for the button-activated medicament delivery device during medicament delivery. Moreover, the processing circuitry is configured to generate a time of measurement, i.e. a time stamp, of the vibration measurement in case the vibration measurement matches the reference vibration measurement. The time of measurement generated may for example be the time and date when the vibration measurement was performed, or it may be the time elapsed since the last use in the event of a multi-use button-activated medicament delivery device. In this manner it may essentially be ensured that each occurrence of drug administration may be registered.

A general example of a button-activated medicament delivery device 1 will now be described with reference to the block diagram in FIG. 1. The button-activated medicament delivery device 1 has a housing, not shown in FIG. 1, arranged to accommodate a medicament container, a button 3 arranged to initiate medicament delivery from the medicament container, a vibration sensor 5 activated by the button 3 and arranged to measure vibrations induced by the button-activated medicament delivery device 1 during a medicament delivery, and processing circuitry 7. As previously mentioned, the processing circuitry 7 is configured to compare a vibration measurement obtained from the vibration sensor 5 with a reference vibration measurement characteristic for the button-activated medicament delivery device during medicament delivery 1.

The processing circuitry 7 may for example be configured to compare amplitude and frequency content of the vibration measurement with amplitude and frequency content of the reference vibration measurement when comparing the vibration measurement with the reference vibration measurement.

The processing circuitry 7 is furthermore configured to generate a time of measurement of the vibration measurement in case the vibration measurement matches the reference vibration measurement. A match may for example be determined if the difference between selected parameters obtained from the vibration measurement and the reference vibration measurement is smaller than a predetermined threshold. This may for example include finding certain characteristic frequency peaks of the frequency spectrum of the vibration measurement, and/or a determining that the differences between the amplitudes of these frequency peaks and the corresponding amplitudes of the reference vibration measurement fall below predetermined thresholds.

The processing circuitry 7 uses any combination of one or more of a suitable central processing unit (CPU), multiprocessor, microcontroller, digital signal processor (DSP), application specific integrated circuit (ASIC), field programmable gate arrays (FPGA) etc., capable of executing any herein disclosed operations.

The button-activated medicament delivery device 1 may furthermore according to one variation include a storage unit 9 configured to store the time of measurement, or time stamp, generated by the processing circuitry 7. The storage unit 9 is hence communicatively coupled to the processing circuitry 7. Thereby, each instance of multiple instances of drug administration may be stored in the storage unit 9.

The button-activated medicament delivery device 1 may furthermore according to one variation include a transmitter 11 arranged to wirelessly transmit the time of measurement generated by the processing circuitry 7. The transmitter 11 may for example be configured to send the time of measurement to a smart phone, tablet computer or to a personal computer. The transmitter 11 hence includes an antenna, which may be arranged to transmit the time of measurement over for example Bluetooth®, Wi-Fi™ or a cellular radio access network (RAN) such as Wideband Code Division Multiple Access (WCDMA) Long Term Evolution (LTE) and the 5G standard.

The button-activated medicament delivery device 1 may furthermore comprise an energy storage unit 15. The energy storage unit 15 may be configured to power the vibration sensor 5, and any other electronic component such as the processing circuitry 7, and the transmitter 11, if present. The energy storage unit 15 may for example be a battery.

The button-activated medicament delivery device 1 may also include an activation switch 13, arranged to be actuated by the button 3. The button 3 is arranged to switch the activation switch 13 between a closed state and an open state. In particular, in a default position, or normal state, of the button 3, the activation switch 13 is in the open state. In the open state the vibration sensor 5 is disconnected from the energy storage unit 15. When the button 3 is pushed to initiate medicament delivery the button 3 sets the activation switch 13 in the closed state. In the closed state the vibration sensor 5 is connected to the energy storage unit 15.

The button 3, the vibration sensor 5 and the processing circuitry 7 form part of an activation button assembly. The storage unit 9, the transmitter 11, the activation switch 13 and the energy storage unit 15 may also form part of the activation button assembly. Examples of activation button assemblies will be described with reference to FIGS. 3-5b.

Figure 2A:
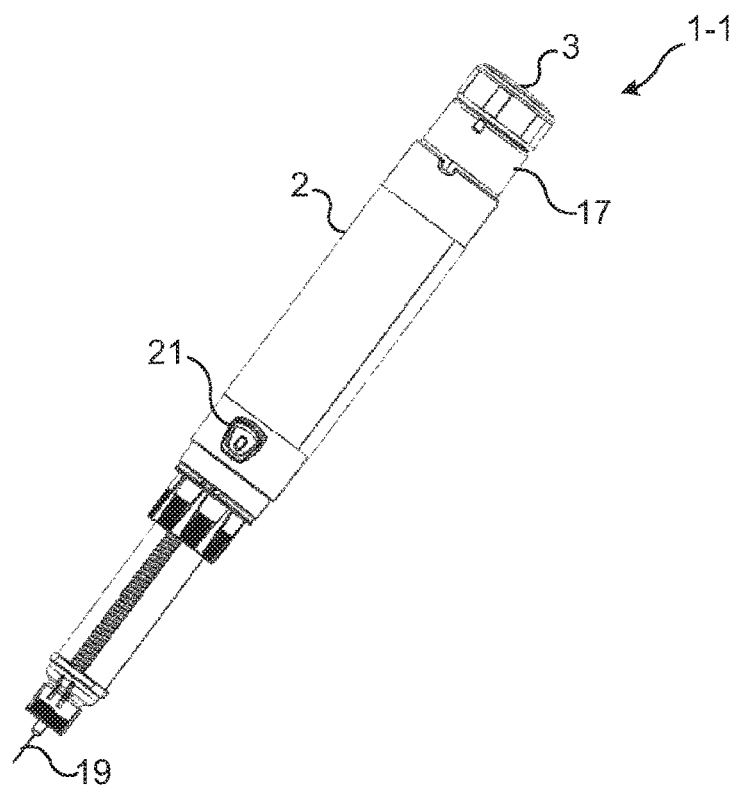
FIG. 2a shows a perspective view of one example of a button-activated medicament delivery device.

FIG. 2a shows one example of a button-activated medicament delivery device. Button-activated medicament delivery device 1-1 comprises a housing 2, a plunger rod 17 movable relative to the housing 2, and an activation button assembly, including button 3 visualised in FIG. 2a.

According to this example, the button-activated medicament delivery device 1-1 is an injector. When the button 3 is pressed with sufficient force, medicament delivery is initiated. In particular, the plunger rod 17 is pressed into the medicament container whereby the medicament contained therein is expelled through the needle 19. Concurrently herewith, the button 3 activates the vibration sensor 5 which starts to measure vibrations in the button-activated medicament delivery device 1. The button-activated medicament delivery device 1-1 also includes a spring-biased dose-setting member 21 which is arranged to rotate as the plunger rod 17 is pushed into the medicament container thereby resetting the dose-indicator. This rotation from start position to final position of the dose-setting member 21 is an example of mechanical interaction that induces vibrations in the button-activated medicament delivery device 1-1. These vibrations are measured by the vibration sensor 5. The vibration measurement is thereafter passed to the processing circuitry 7 for comparison with a reference vibration measurement for this particular button-activated medicament delivery device 1-1 obtained during a reference medicament delivery procedure.

Another example of a button-activated medicament delivery device that makes "click" sounds is of the kind that has a needle shield or needle cover that automatically locks out after the drug administration has been finalised to protect the user from the needle and to prevent reuse of the button-activated medicament delivery device. An example of a medicament delivery device with this functionality is disclosed in WO2011005177. This document also discloses a realisation of an end-of-injection feedback.

The button may also be arranged at other locations than the distal end relative to the expulsion side of the button-activated medicament delivery device, for instance on the side of the housing, as for example disclosed in WO2014029621.

Figure 2B:
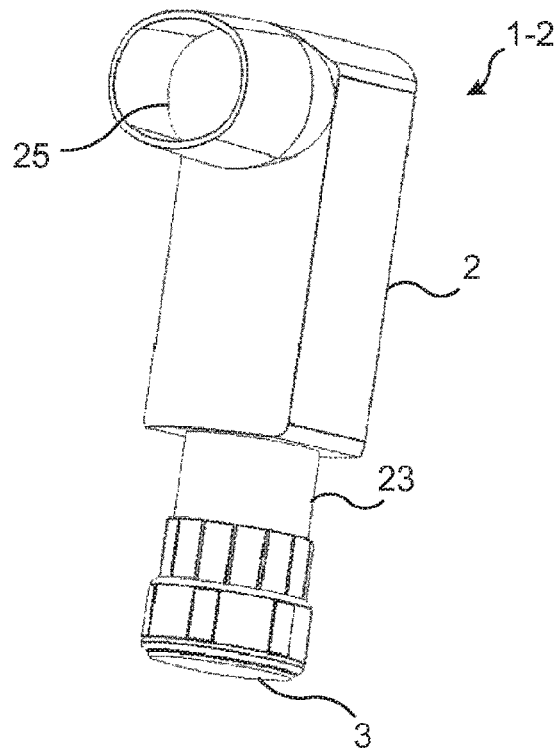
FIG. 2b shows a perspective view of another example of a button-activated medicament delivery device.

FIG. 2b shows another example of a button-activated medicament delivery device, namely an inhaler. Button-activated medicament delivery device 1-2 comprises a housing 2, a medicament container 23, an activation button assembly, including button 3 visualised in FIG. 2b, and a mouthpiece 25. The activation button assembly is provided on the medicament container 23. When the button 3 is pressed with sufficient force, the content of the medicament container 23 is expelled through the mouthpiece 25. In this case, there is a characteristic sound created during the medicament expulsion. The vibrations caused by this sound are measured by the vibration sensor activated by the button 3 upon initiation of the medicament delivery. Comparison by the processing circuitry is performed in the same manner as has previously been described.

Figure 3:
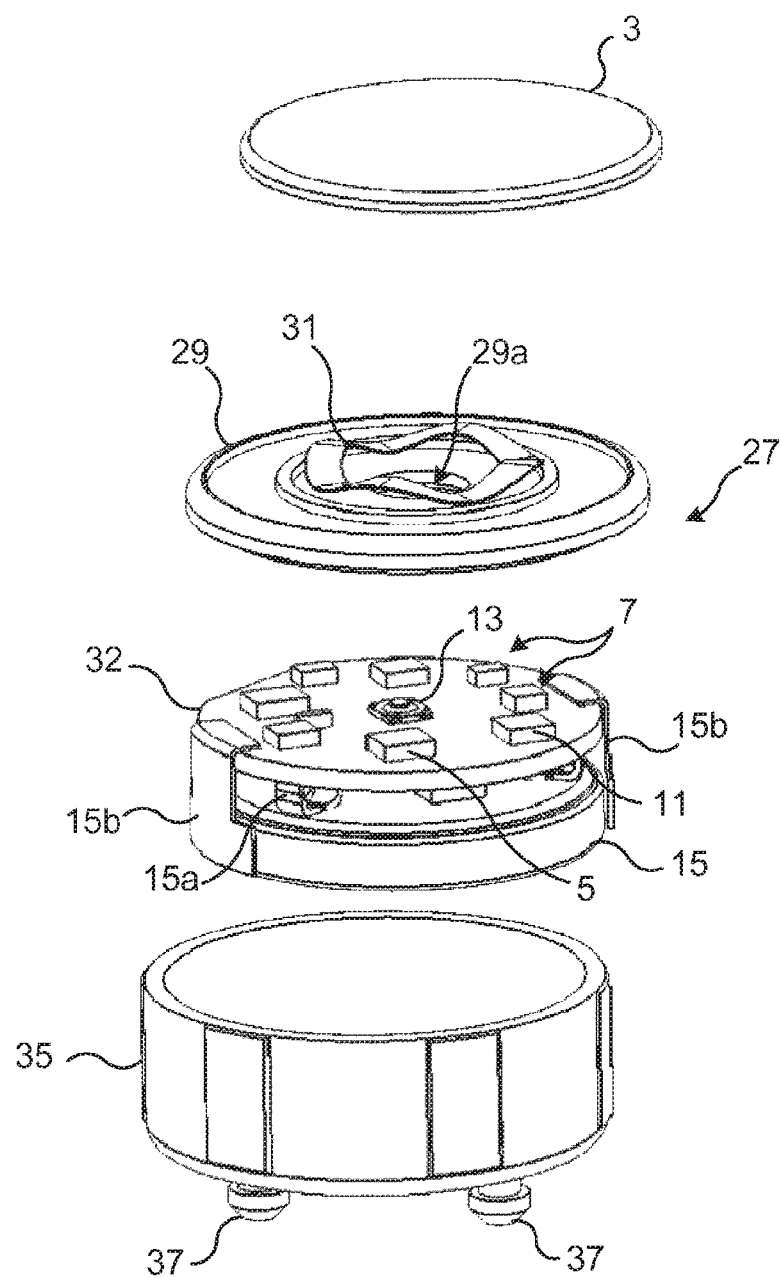
FIG. 3 shows an example of an activation button assembly of a button-activated medicament delivery device.

FIG. 3 shows an example of an activation button assembly 27. According to this example, the button-activated medicament delivery device furthermore includes an energy accumulation member 31, such as a button spring, a plate member 29, and a circuit board 32 on which the vibration sensor 5 and the processing circuitry 7 are mounted. This example also comprises the energy storage unit 15, in the form of a battery, first electrodes 15a defining a first electric pole, and second electrodes 15b defining a second electric pole. The first electrodes 15a and the second electrodes are connected to the energy storage unit 15.

The energy storage unit 15 is arranged parallel with the circuit board 32, and in particular with the plane defined by the circuit board 32. The first electrodes are placed between the energy storage unit 15 and the circuit board 32, acting as spacers or distancing members. This enables two-sided mounting of electronic components onto the circuit board 32. Moreover, it can increase the range of the transmitter in variations of the activation button assembly 27 that includes a transmitter. The activation button assembly 27 may hence also comprise transmitter 11.

The processing circuitry 7 may also include a clock crystal in order to manage the time-keeping of the vibration measurements.

Figure 4A:
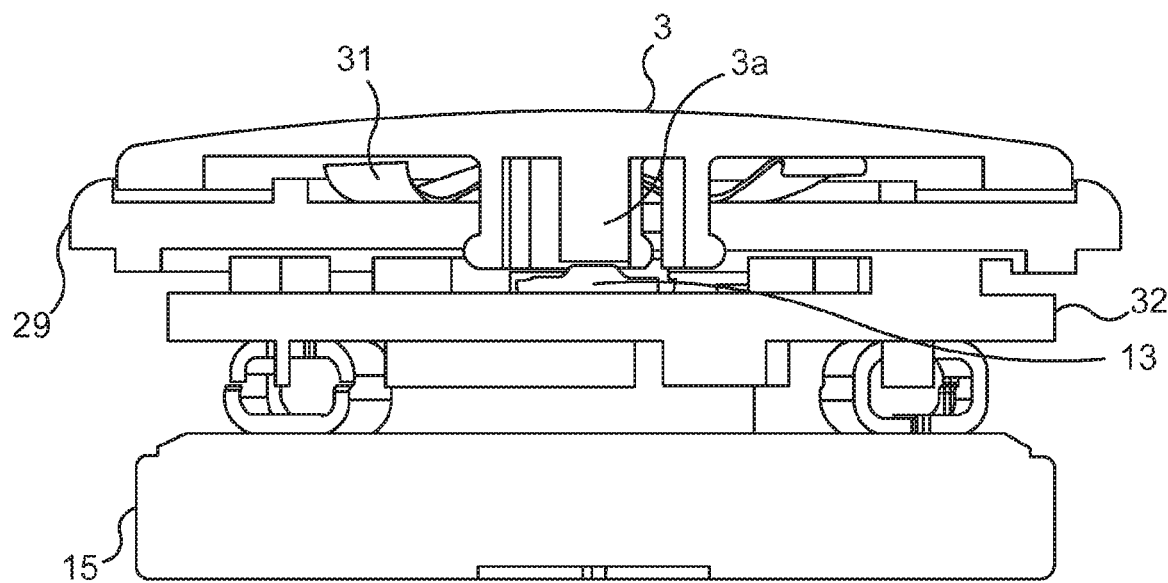
FIGS. 4a and 4b show cross sections of the activation button assembly in FIG. 3 when the activation switch is in the open state and when the activation switch is in the closed state, respectively.
Figure 4B:
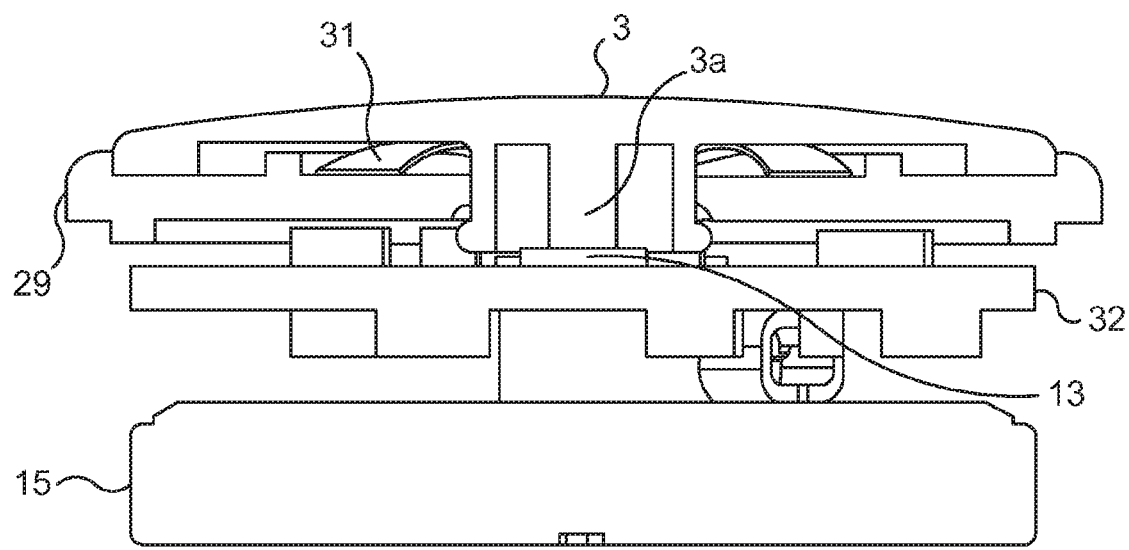

The plate member 29 may be arranged in parallel with the circuit board 32, on the opposite side of the circuit board 32 relative to the energy storage unit 15. The plate member 29 may have a through-hole 29a aligned with the activation switch 13 mounted on the circuit board 32, and the button 3 may have an actuation member 3a, as shown in FIGS. 4a-b, aligned with and arranged to extend through the through-opening 29a, thereby enabling actuation of the activation switch 13 when the button 3 is pushed towards the circuit board 32.

The energy accumulation member 31 is arranged between the button 3 and the plate member 29. The energy accumulation member 31 is arranged to bias the button 3 away from the activation switch 13. Thus, in a default state, the activation member of the button 3 is distanced from the activation switch 13, as shown in FIG. 4a. When the button 3 is pressed with sufficient force, the energy accumulation member is temporarily deformed as it receives energy from the pressure applied by the button 3, wherein the actuation member contacts and actuates the activation switch 13. This results in the activation of the vibration sensor 5, as it is connected to the energy storage unit 15. This is shown in FIG. 4b.

Figure 5A:
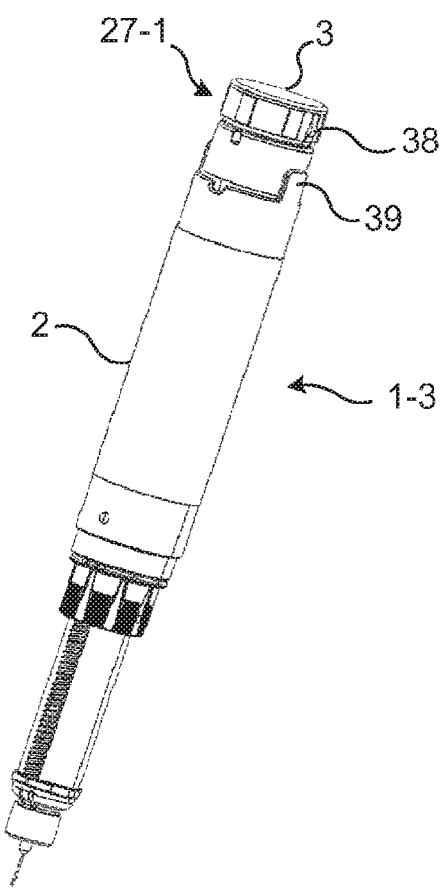
FIGS. 5a-c show another example of an activation button assembly.
Figure 5B:
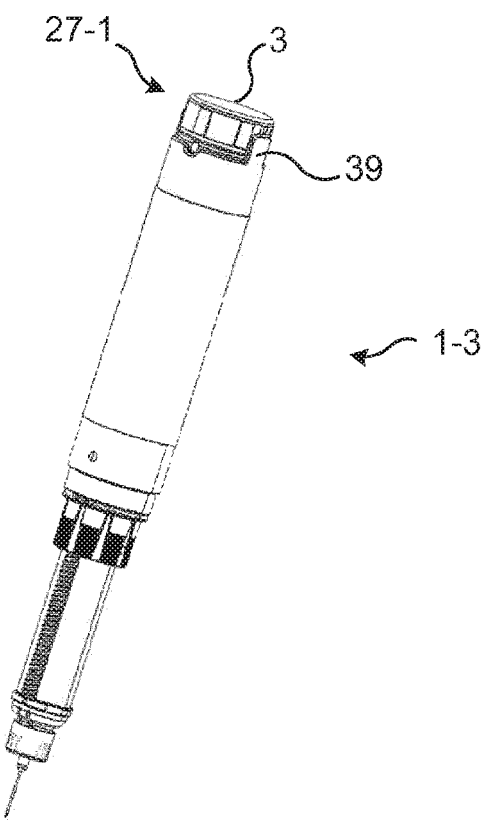
Figure 5C:
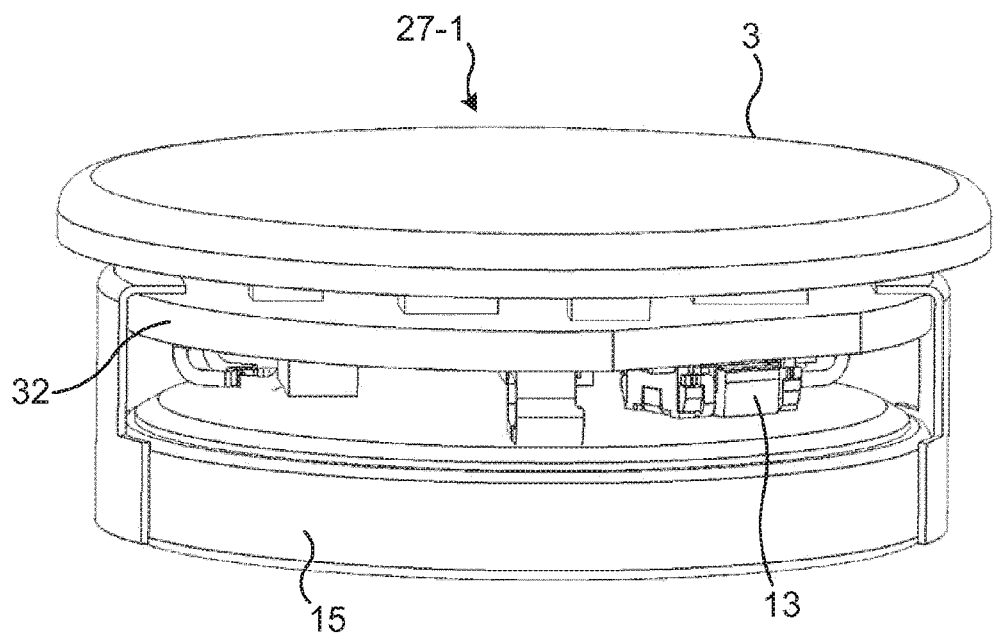

FIG. 5a shows a button-activated medicament delivery device 1-3 that includes an activation button assembly 27-1 similar to the one described with reference to FIG. 3. The button-activated medicament delivery device 1-3 has a tongue 39 arranged to interact with the activation button assembly 27-1. The tongue 39 may be provided on the housing 2 of the button-activated medicament delivery device 1-3. The activation button assembly 27-1 has a flexible radially extending portion 38. When the button 3 is pressed such that medicament delivery is initiated, as shown in FIG. 5b, the flexible radially extending portion 38 is pressed radially inwards by the tongue 39. The vibration sensor is thereby activated. The vibration sensor is in particular activated by the flexible radially extending portion 38 which sets the activation switch in the closed state. The flexible radially extending portion 38 hence acts as an actuation member arranged to actuate the activation switch between the open state and the closed state. FIG. 5c shows the activation switch 13 which in this case is arranged aligned with and radially inwards of the flexible radially extending portion 38, which itself is not shown in FIG. 5c.

The activation button assembly 27, 27-1 may either be an integrated part of a button-activated medicament delivery device or it may be releaseably arranged relative to the remainder of the button-activated medicament delivery device, as shown in the example in FIG. 3. To this end, the activation assembly 27, 27-1 may be mounted in an activation button assembly housing 35 that is attachable to the remainder of a button-activated medicament delivery device. This may for example be achieved by means of a keyhole interface 37 that includes locking knobs.

The activation button assembly 27, 27-1 may be associated with a unique identifier such that time of measurements, or time stamps, obtained from the activation button assembly 27, 27-1 may be associated with a specific user. The processing circuitry 7 may hence be configured to associate the time stamps with the identifier. In case the activation button assembly 27, 27-1 is integrated with the button-activated medicament delivery device, the identifier may also be associated with the button-activated medicament delivery device. In variations in which the activation button assembly 27, 27-1 is releasable, the identifier may be an identifier which only identifies the activation button assembly 27, 27-1, since it may be mounted to different button-activated medicament delivery devices.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A button-activated medicament delivery device comprising:
    a housing arranged to house a medicament container, and
    a button assembly operatively connected to the housing, where the button assembly comprises:
        an assembly housing;
        a button movable relative to the housing and the assembly housing, where movement of the button causes medicament to be expelled from the medicament container;
        a button spring operatively connected to the button that biases the button in an extended position relative to the assembly housing;
        a switch having an open state and a closed state, where the switch is in the open state when button is in the extended position;
        a vibration sensor configured to measure vibrations induced by the button-activated medicament delivery device during a medicament delivery,
        processing circuitry configured to obtain a vibration measurement from the vibration sensor and to compare the vibration measurement with a reference vibration measurement characteristic for the button-activated medicament delivery device during medicament delivery, and
        an energy storage unit that supplies energy to the vibration sensor and processing circuitry when the switch is in the closed position;
    wherein the processing circuitry is configured to generate a time of measurement of the vibration measurement in case the vibration measurement matches the reference vibration measurement.

2. The button-activated medicament delivery device as claimed in claim 1, comprising a storage unit configured to store the time of measurement.

3. The button-activated medicament delivery device as claimed in claim 1, comprising a transmitter configured to wirelessly transmit the time of measurement.

4. The button-activated medicament delivery device as claimed in claim 1, wherein when the button is in the closed state upon initiation of medicament delivery.

5. The button-activated medicament delivery device as claimed in claim 1, wherein the processing circuitry is configured to compare amplitude and frequency content of the vibration measurement with amplitude and frequency content of the reference vibration measurement.

6. The button-activated medicament delivery device as claimed in claim 1, comprising a circuit board arranged parallel to the energy storage unit, a first electrode defining a first electric pole and a second electrode defining a second electric pole, wherein the first electrode distances the circuit board from the energy storage unit.

7. The button-activated medicament delivery device as claimed in claim 1, comprising a plate member having a through-opening, which plate member is arranged between the circuit board and the button, wherein the button spring is arranged between the plate member and the button.

8. The button-activated medicament delivery device as claimed in claim 7, wherein the switch is aligned with the through-opening of the plate member and wherein the button has an actuation member aligned with the through-opening, which actuation member is arranged to actuate the switch.

9. The button-activated medicament delivery device as claimed in claim 1, wherein the button assembly is releasably attached to a portion of the button-activated medicament delivery device.

10. The button-activated medicament delivery device as claimed in claim 1, wherein the vibration sensor includes an acceleration sensor.

11. The button-activated medicament delivery device as claimed in claim 1, wherein the button-activated medicament delivery device is an injector.

12. The button-activated medicament delivery device as claimed in claim 11, comprising a plunger rod, wherein the vibration sensor, the button and the processing circuitry form part of the plunger rod.

13. The button-activated medicament delivery device as claimed in claim 1, wherein the button activated medicament delivery device is an inhalator or an eye dispenser.

* * * * *